United States Patent [19]

Ayres

[11] 4,168,309

[45] Sep. 18, 1979

[54] CEPHALOSPORINS HAVING A 7-(CARBOXY SUBSTITUTED α-ETHERIFIED OXIMINOARYLACETAMIDO) GROUP

[75] Inventor: Barry E. Ayres, Ickenham, England

[73] Assignee: Glaxo Laboratories Limited, Greenford, England

[21] Appl. No.: 838,366

[22] Filed: Sep. 30, 1977

[30] Foreign Application Priority Data

Oct. 1, 1976 [GB] United Kingdom ............... 40919/76

[51] Int. Cl.$^2$ .................. A61K 31/545; C07D 501/40
[52] U.S. Cl. ...................... 424/246; 544/22; 544/24; 544/25; 544/26; 544/27
[58] Field of Search ............. 544/27, 22, 24, 25, 544/26; 424/246

[56] References Cited

U.S. PATENT DOCUMENTS 4,074,047  2/1978  Foxton et al. ............... 544/27
4,095,021  6/1978  Bradshaw et al. ............ 544/27

FOREIGN PATENT DOCUMENTS 2460537  3/1975  Fed. Rep. of Germany.

Primary Examiner—David Wheeler
Attorney, Agent, or Firm—Bacon & Thomas

[57] ABSTRACT

Antibiotic compounds of the general formula

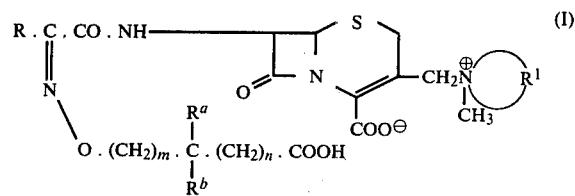

[wherein R is a phenyl, thienyl or furyl group; $R^a$ and $R^b$ which may be the same or different, are each selected from hydrogen, $C_{1-4}$ alkyl, $C_{2-4}$ alkenyl, $C_{3-7}$ cycloalkyl, phenyl, naphthyl, thienyl, furyl, carboxy, $C_{2-5}$ alkoxycarbonyl and cyano, or $R^a$ and $R^b$ together with the carbon atom to which they are attached form a $C_{3-7}$ cycloalkylidene or cycloalkenylidene group; m or n are each 0 or 1 such that the sum of m and n is 0 or 1; and $R^1$ together with the nitrogen atom to which it is attached form a saturated or partially saturated 4–10 membered heterocyclic ring which may contain one or more further heteroatoms selected from O,N and S and which may be substituted by a lower alkyl, lower alkoxy, lower acyloxy, lower alkoxycarbonyl, hydroxy, carboxy, amino, acylamino, substituted or unsubstituted carbamoyl or aryl group, or such a heterocyclic ring fused with a benzene ring] and non-toxic derivatives thereof, the compounds being syn isomers or existing as mixtures of syn and anti isomers.

17 Claims, No Drawings

CEPHALOSPORINS HAVING A 7-(CARBOXY SUBSTITUTED α-ETHERIFIED OXIMINOARYLACETAMIDO) GROUP

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after *J.Amer.-Chem.Soc.*, 1962, 84, 3400, the term "cephem" referring to the basic cepham structure with one double bond.

Cephalosporin antibiotics are widely used in the treatment of diseases caused by pathogenic bacteria in humam beings and animals, for example in the treatment of diseases caused by bacteria which are resistant to other antibiotics such as penicillin compounds and in the treatment of penicillin-sensitive patients. In many instances it is desirable to employ a cephalosporin antibiotic which exhibits activity against both gram positive and gram negative microorganisms and a significant amount of research has been directed to the development of various types of broad spectrum cephalosporin antibiotics.

Considerable interest is currently being directed to the development of broad spectrum cephalosporin antibiotics which possess high activity against gram negative organisms. Existing commercially available β-lactam antibiotics tend to exhibit comparatively low activity against certain gram negative organisms such as Proteus organisms, which are increasingly common source of infection in humans, and are also generally substantially inactive against strains of *Pseudomonas aeruginosa* organisms. It is well known that cephalosporin antibiotics normally exhibit low toxicity in man, so that the development of broad spectrum cephalosporin antibiotics possessing high activity against gram negative organisms such as many strains of Proteus and *Pseudomonas aeruginosa* fulfils a significant need in chemotherapy.

According to one aspect of the present invention we provide antibiotic compounds of the general formula

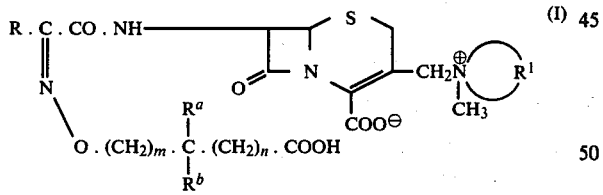

[wherein R is a phenyl, thienyl or furyl group; $R^a$ and $R^b$, which may be the same or different, are each selected from hydrogen, $C_{1-4}$ alkyl (e.g. methyl, ethyl, n-propyl, isopropyl or butyl), $C_{2-4}$ alkenyl (e.g. vinyl or allyl), $C_{3-7}$ cycloalkyl (e.g. cyclopropyl, cyclobutyl, cyclopentyl or cyclohexyl), phenyl, naphthyl, thienyl, furyl, carboxy, $C_{2-5}$ alkoxycarbonyl (e.g. ethoxycarbonyl) and cyano, or $R^a$ and $R^b$ together with the carbon atom to which they are attached form a $C_{3-7}$ cycloalkylidene or cycloalkenylidene group (e.g. a cyclobutylidene, cyclopentylidene or cyclohexylidene group); m or n are each 0 or 1 such that the sum of m and n is 0 or 1; and $R^1$ together with the nitrogen atom to which it is attached form a saturated or partially saturated 4–10 membered heterocyclic ring which may contain one or more further heteroatoms selected from O,N and S and which may be substituted by a lower alkyl (e.g. $C_{1-4}$ alkyl), lower carboxylic alkoxy (e.g. $C_{1-4}$ alkoxy), lower acyloxy (e.g. $C_{2-5}$ acyloxy), lower alkoxycarbonyl (e.g. $C_{2-5}$ alkoxycarbonyl), hydroxy, carboxy, amino, acylamino, substituted or unsubstituted carbamoyl or aryl (e.g. phenyl) group, or such a heterocyclic ring fused with a benzene ring] and non-toxic derivatives thereof, the compounds being syn isomers or existing as mixtures of syn and anti isomers.

These compounds exhibit broad spectrum antibiotic activity characterised by particularly high activity against gram negative microorganisms, including those which produce β-lactamases, and also possess very high stability to β-lactamases produced by a range of gram negative organisms. A particular advantage of the compounds is their high in vitro activity against β-lactamase-producing gram-negative organisms, especially strains of *Escherichia coli, Enterobacter cloacae, Klebsiella aerogenes, Haemophilus influenzae* and Proteus species (such as strains of *Proteus morganii* and *Proteus mirabilis*). Compounds wherein at least one of $R^a$ and $R^b$ is other than hydrogen have also shown high activity against strains of *Pseudomonas aeruginosa*.

The compounds of formula I are thus useful for treating a variety of diseases caused by pathogenic bacteria such as respiratory tract or urinary tract infections.

The compounds of the invention are defined as having the syn isomeric form as regards the configuration of the group

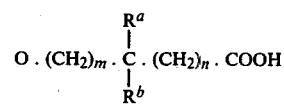

with respect to the carboxamido group. In this specification the syn configuration is denoted structurally as

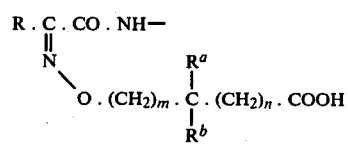

this configuration being assigned on the basis of the work of Ahmad and Spenser reported in *Can.J. Chem.*, 1961, 39, 1340. As indicated above, the compounds may exist as mixtures of syn and anti isomers. Such mixtures may contain at least 75% of the syn isomer. We prefer, however, the compounds to be syn isomers essentially free from the corresponding anti isomer.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that derivatives such as salts and esters may be formed by reaction of either or both of the carboxyl groups present in the compounds of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, toluene-p-sulphonic and methane sulphonic acids. Where insoluble salts of compounds (I) are desired in a particular application, e.g. for use in depot preparations, such salts may be formed in conventional manner, for example with appropriate organic amines.

Biologically acceptable, metabolically labile ester derivatives which may be formed of compounds of formula I include, for example, acyloxymethyl esters, e.g. lower alkanoyloxymethyl esters such as acetoxymethyl or pivaloyloxymethyl esters.

Where the group R in the above formulae is a furyl group it may be fur-2-yl or fur-3-yl and where it is a thienyl group it may be thien-2-yl or thien-3-yl.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisomeric. The invention embraces the individual diastereoisomers of such compounds as well as mixtures thereof.

Preferred compounds according to the invention by virtue of their especially good antibiotic activity against strains of various gram negative organisms include those compounds of formula I wherein m and n are 0, $R^a$ is hydrogen, methyl, ethyl, propyl, allyl or phenyl and $R^b$ is carboxy or a group as defined for $R^a$; or $R^a$ and $R^b$ together with the carbon atom to which they are attached form a cyclobutylidene, cyclopentylidene or cyclohexylidene ring. In such compounds the group $R^1$ together with the nitrogen atom to which it is attached preferably represents a saturated or mono-unsaturated 5-, 6-, 7- or 8-membered heterocyclic ring containing, if desired, a further nitrogen or oxygen heteroatom and being substituted, if desired, by a methyl, carbamoyl, ethoxycarbonyl, acetoxy or phenyl group. The heterocyclic ring may also be fused with a benzene ring. The group R is preferably a fur-2-yl group.

Preferred compounds according to the invention include salts of the following cations:

(6R,7R)-7-[2-(2-carboxyprop-2-yloxyimino)-2-(fur-2-yl)acetamido]-3-[(4-ethoxycarbonyl-1-methyl-1-piperazinium) methyl]ceph-3-em-4-carboxylic acid (syn isomer), (6R,7R)-7-[2-(2-carboxyprop-2-yloxyimino)-2-(fur-2-yl) acetamido]-3-(1-methyl-1-hexamethyleneiminiummethyl)ceph-3-em-4-carboxylic acid (syn isomer), (6R,7R)-7-[2-(2-carboxyprop-2-yloxyimino)-2-(fur-2-yl) acetamido]-3-[(1,4-dimethyl-1-piperidinium)methyl]-ceph-3-em-4-carboxylic acid (syn isomer), (6R,7R)-[2-(2-carboxyprop-2-yloxyimino)-2-(fur-2-yl) acetamido]-3-[(3-carbamoyl-1-methyl-1-piperidinium)methyl]ceph-3-em-4-carboxylic acid (syn isomer), (6R,7R)-7-[2-(2-carboxyprop-2-yloxyimino)-2-(fur-2-yl) acetamido]-3-(1-methyl-1,2,3,6-tetrahydropyridinium-1-ylmethyl)ceph-3-em-4-carboxylic acid (syn isomer), (6R,7R)-7-[2-(2-carboxyprop-2-yloximino)-2-(fur-2-yl) acetamido]-3-(4-acetoxy-1-methyl-1-piperidiniummethyl) ceph-3-em-4-carboxylic acid (syn isomer), (6R,7R)-7-[2-(2-carboxyprop-2-yloximino)-2-(fur-2-yl)acetamido]-3-(4-carbamoyl-1-methyl-1-piperidiniummethyl)-ceph-3-em-4-carboxylic acid (syn isomer), and (6R,7R)-7-[2-(2-carboxyprop-2-yloxyimino)-2-(fur-2-yl)acetamido]-3-(1-methyloctahydroazocinium-1-ylmethyl)ceph-3-em-4-carboxylic acid (syn isomer).

Two particularly preferred compounds are:

(6R,7R)-7-[2-(2-carboxyprop-2-yloximino)-2-(fur-2-yl) acetamido]-3-[1-methyl-pyrrolidinium-1-ylmethyl]-ceph-3-em-4-carboxylic acid (syn isomer), and (6R,7R)-7-[2-(1-carboxycyclobut-1-yloximino)-2-(fur-2-yl) acetamido]-3-(1,4-dimethylpiperidinium-1-ylmethyl)ceph-3-em-4-carboxylic acid (syn isomer).

The compounds according to the invention may be prepared by any convenient method, for example by techniques analogous to those described in British Pat. No. 1326531.

Thus according to a further aspect of the invention we provide a process for the preparation of an antibiotic compound of formula I as hereinbefore defined or a non-toxic derivative thereof which comprises (A) reacting a compound of formula

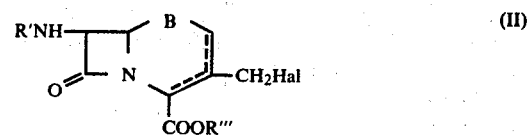

(II)

[wherein R''' is a carboxyl blocking group, Hal is halogen, preferably bromine, B is S or S→O, preferably S→O and the dotted line indicates the double bond may be in the 2,3 or 3,4 position, except that B is not S→O when the double bond is in the 2,3-position, and R' is a group of formula

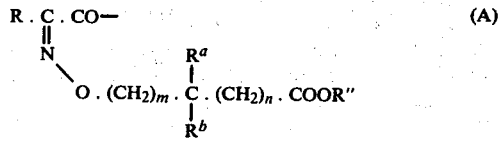

(A)

(wherein R, $R^a$, $R^b$, m and n are as hereinbefore defined and R'' is also a carboxyl blocking group) or a precursor therefor] or a compound of formula

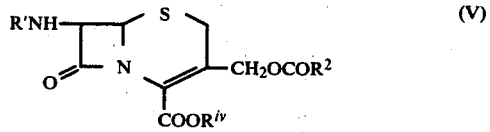

(V)

[wherein R' is as hereinbefore defined and $R^{iv}$ is H or a carboxyl blocking group and $R^2$ is the residue of a dicarboxylic acid e.g. haloacetic acid] with a secondary amine of formula

(III)

(wherein $R^1$ is as hereinbefore defined) and subsequently reacting the product with a methylating agent, eg a methyl halide, preferably methyl iodide; or (B) reacting the said compound of formula II or V with a tertiary amine of formula

(IV)

(wherein $R^1$ is as hereinbefore defined); or (C) condensing a compound of formula

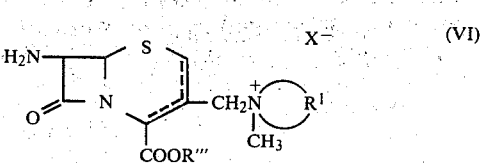

(wherein $R^1$, and $R'''$ are as hereinbefore defined, $X^-$ represents an anion, and the dotted line bridging the 2,3 and 4-positions indicates that the compound may be a ceph-2-em or a ceph-3-em compound) or a salt, e.g. an acid addition salt such as hydrochloride, hydrobromide, sulphate, nitrate, phosphate, methane sulphonate or tosylate, or an N-silylated derivative thereof, with an acylating agent corresponding to an acid of formula

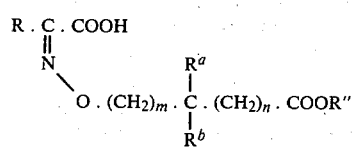

(wherein R, $R^a$, $R^b$, $R''$, m and n are as hereinbefore defined) or with a precursor therefor; whereafter, if necessary and/or desired in each instance any of the following reactions (D) in any appropriate sequence are carried out:

(i) reduction of a sulphoxide group to a sulphide group;
(ii) conversion of a precursor for the group (A) to that said group;
(iii) removal of any carboxyl blocking groups; and
(iv) conversion of a $\Delta^2$ compound to a $\Delta^3$ compound; and finally (E) recovering the desired compound of formula I or non-toxic derivative thereof.

Non-toxic derivatives of the compounds of formula I may be formed in any convenient way, for example according to methods well known in the art. Biologically acceptable ester derivatives may be formed using conventional esterifying agents.

1-Oxides may be formed by treatment of the corresponding cephalosporin sulphide with an appropriate oxidising agent, for example with a peracid.

The displacement of Hal in compounds of formula (II) by the amine of formula (III) or (IV) may conveniently be effected by maintaining the reactants in solution or suspension at a moderate temperature, e.g. from $-40°$ to $+130°$ C., preferably from $0°$ to $60°$ C., conveniently at about $25°$ C.

The reaction is advantageously effected using from one to three molar equivalents of amine (III) or (IV) and is preferably carried out in an organic solvent and under anhydrous conditions. Organic media which may be used include lower alkanoic acid nitriles e.g. acetonitrile or propionitrile; halogenated hydrocarbons e.g. methylene chloride, chloroform, ethylene dichloride or perchloroethylene; hydrocarbons e.g. benzene; cyclic ethers e.g. dioxan or tetrahydrofuran; amide solvents e.g. N,N-dimethylformamide; di-lower alkyl sulphoxides, e.g. dimethylsulphoxide; esters, e.g. ethyl acetate; and ketones e.g. acetone. The displacement of 52 O.-$COR^2$ in compounds of formula (V) where $R^{iv}=H$ by the amine of formula (III) or (IV) may conveniently be effected in solution, preferably in a polar medium, again at a moderate temperature, e.g. from $0°$ to $120°$ C., preferably from $35°$ to $75°$ C., advantageously at about $50°$ C.

When using an amine of formula (IV) the reaction product may be separated from the reaction mixture, which may contain, for example, unchanged cephalosporin and other substances, by a variety of processes including precipitation, trituration, or by chromatography on ion-exchange resins. When using an amine of formula (III) the reaction product may be isolated by chromatography on silica, by precipitation or by solvent extraction. This product is subsequently quaternised by reaction with a methylating agent e.g. a methyl halide, preferably methyl iodide, preferably under anhydrous conditions. An organic solvent such as N,N-dimethylformamide, chloroform or tetrahydrofuran may be employed but preferably the methyl iodide itself serves as solvent.

After the introduction of the quaternary ammonium group the 1-sulphinyl group may be reduced by any convenient means. This may, for example, be effected by reduction of the corresponding acyloxysulphonium or alkyloxysulphonium salt prepared in situ by reaction with e.g. acetyl chloride in the case of an acetoxy-sulphonium salt, reduction being effected by, for example, sodium dithionite or by iodide ion as in a solution of potassium iodide in a water miscible solvent e.g. acetone, tetrahydrofuran, dioxan, dimethylformamide or dimethylacetamide. The reaction may be effected at a temperature of $-20°$ to $+50°$ C., preferably at about $0°$ C.

Acylating agents which may be employed in the preparation of compounds of formula I include acid halides, particularly acid chlorides or bromides. Such acylating agents may be prepared by reacting an acid (VII) or a salt thereof with a halogenating agent e.g. phosphorus pentachloride, thionyl chloride or oxalyl chloride. Treatment of the sodium, potassium or triethylammonium salt of the acid (VII) with oxalyl chloride is advantageous in that under these conditions isomerisation is minimal.

Acylations employing acid halides may be effected in aqueous and non-aqueous reaction media, conveniently at temperatures of from $-50°$ to $+50°$ C., preferably $-20°$ to $+30°$ C., if desired in the presence of an acid binding agent. Suitable reaction media include aqueous ketones such as aqueous acetone, esters such as ethyl acetate, halogenated hydrocarbons such as methylene chloride, amides such as N,N-dimethylacetamide, nitriles such as acetonitrile, or mixtures of two or more such solvents. Suitable acid binding agents include tertiary amines (e.g. triethylamine or N,N-dimethylaniline), inorganic bases (e.g. calcium carbonate or sodium bicarbonate), and oxiranes such as lower 1,2-alkylene oxides (e.g. ethylene oxide or propylene oxide) or molecular sieves which bind hydrogen halide liberated in the acylation reaction.

Acids of formula VII may themselves be used as acylating agents in the preparation of compounds of formula I. Acylations employing acids (VII) are desirably conducted in the presence of a condensation agent, for example a carbodiimide such as N,N'-dicyclohexylcarbodiimide; a carbonyl compound such as carbonyldiimidazole; or an isoxazolinium salt such as N-ethyl-5-phenylisoxazolinium perchlorate. Acylation reactions of this type are desirably effected in an anhydrous reaction medium, e.g. methylene chloride, dimethylformamide or acetonitrile.

Acylation may also be effected with other amide-forming derivatives of acids of formula VII such as, for example, a symmetrical anhydride or a mixed anhydride (e.g. with pivalic acid or formed with a haloformate such as a lower alkylhaloformate). The mixed or symmetrical anhydride may be generated in situ; thus, for example, a mixed anhydride may be generated using N-ethoxycarbonyl-2-ethoxy-1,2-dihydroquinoline. Mixed anhydrides may also be formed with phosphorus acids (for example phosphoric or phorphorous acids), sulphuric acid or aliphatic or aromatic sulphonic acids (for example p-toluene sulphonic acid).

It will be appreciated that in processes for the preparation of compounds of formula I wherein $R^a$ or $R^b$ represents carboxy or the heterocyclic ring carries a carboxy substituent it will in many instances be necessary to protect the carboxy group, for example by substitution with a carboxyl blocking group.

Carboxyl blocking groups $R''$ and $R'''$ used in the preparation of compounds of formula I or in the preparation of necessary starting materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. pivaloyloxymethyl) and retain these in the final product to give a biologically acceptable ester derivative of a compound of formula I.

Suitable carboxyl blocking groups are well known in the art, a list of representative blocked carboxyl groups being included in Belgian Pat. No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

It has been found that if deprotection of the carboxyl group is carried out on a halide salt of the quaternary compound there is a tendency for isomerisation of the oxyimino moiety in the 7β-acylamido side chain to occur and the anti-isomer tends to be the predominant product. This tendency to isomerisation may be substantially lessened by conversion of the halide salt to a non-halide salt, especially the trifluoroacetate, before deprotection takes place, for example by methods analogous to those described in our copending application No. 55213/74.

If the 7β-acylamido group or a substituent on the heterocyclic ring contains any carboxyl, hydroxy or amino groups it is necessary to protect these groups also during the various reaction stages. The protecting groups used are conveniently those which can be removed by hydrolysis without affecting the rest of the molecule, especially the lactam and 7β-amido-linkages. Carboxyl, hydroxy or amine protecting groups and the esterifying group at the 4- COOH position can generally be removed using the same reagent.

According to two preferred embodiments of the invention the preparation of compounds of general formula I and non-toxic derivatives thereof according to the invention may be proceeded with via the following sequence of steps wherein the groups $R^1$, $R^2$, $R'$, $R''$, $R'''$ and X are as hereinbefore defined):

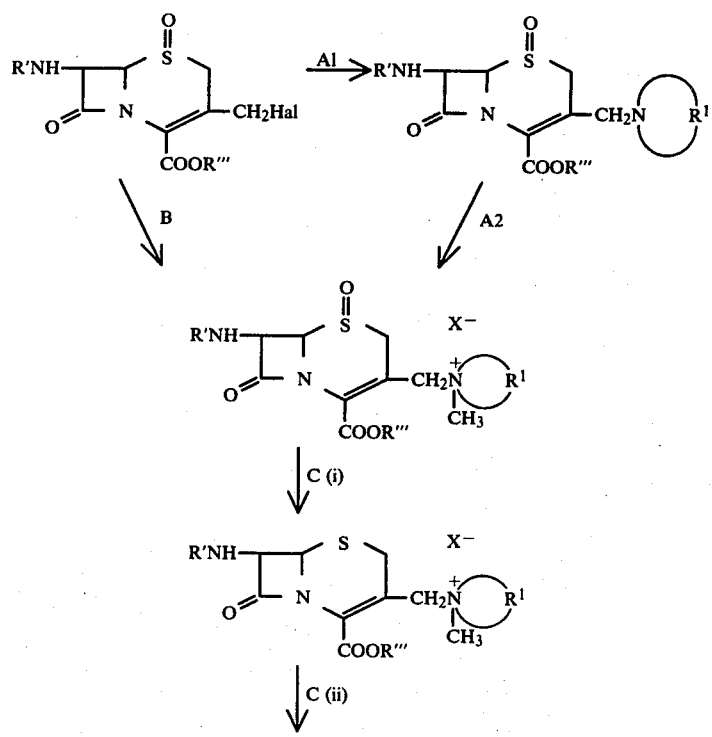

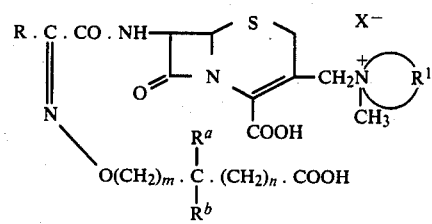

Compounds obtained from step C(ii) may be converted to compounds of formula I in conventional manner by treatment with a base followed, if necessary, by ion-exchange.

Depending on the configuration of the oxyimino group in the starting material used, the compound of formula I or derivative thereof may be obtained as a single isomer or as a mixture of syn and anti isomers. Separation of the isomers is very difficult due to the presence of the quaternary group and if a pure syn isomer is desired it is generally necessary to use a starting material which is entirely in the syn isomeric form. Syn and anti isomers may be separated by appropriate techniques, e.g. by high pressure liquid chromatography, or by thin layer or paper chromatography or distinguished by their proton magnetic resonance spectra. Thus, for example, the p.m.r. spectra of DMSO-$d_6$ solutions of syn compounds of formula I exhibit the doublet for the amide NH at a lower field than do similar solutions of the corresponding anti isomers. These factors may be employed in monitoring reactions.

Starting materials of formula II may, for example, be prepared by condensing a compound of formula

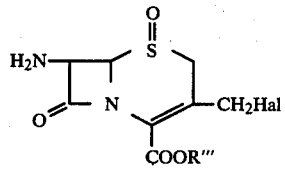

(wherein Hal and R''' are as hereinbefore defined) with an acylating agent corresponding to an acid of formula VII under similar conditions to those described hereinbefore for the acylation of compounds of formula VI. If halogen interchange at the 3-methyl position is desirable, this is effected after the acylation step.

The antibiotic compounds of formula I and non-toxic derivatives thereof according to the invention may be formulated for administration in any convenient way by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The compositions may contain from 0.1% upwards, e.g. 0.1–99%, preferably from 10–60% of the active material, depending on the method of administration. When the compositions comprise dosage units, each unit will preferably contain 250mg to 5g of the active ingredient. The dosage as employed for adult human treatment will preferably range from 500mg to 15g per day, preferably from 1.5 to 3g per day, depending on the route and frequency of administration.

The antibiotic compounds according to the invention may be administered in combination with other therapeutic agents such as antibiotics, for example penicillins, or other cephalosporins.

The following Examples illustrate the invention. All temperatures are in °C. Thin layer chromatography (t.l.c.) was carried out on Merck Kieselgel $F_{254}$ silica plates (0.25 mm) eluted in ethyl acetate (steps a) and b)) or in chloroform/methanol/acetic acid (90:16:20) (step c). Kieselgel $F_{254}$ silica plates are plates coated with silica gel impregnated with a fluorescent (254 nm) indicator. Deacidite FF is a highly basic (strong anion) type of cross-linked polystyrene anion exchange resin (2–3% cross-linking, 52–100 mesh).

Tetrahydrofuran was dried by passage through a column of basic alumina.

The structures of the products were verified by p.m.r. and i.r. spectroscopy.

EXAMPLE 1 (Method A)

(6R,7R)-7-[2-Carboxyprop-2-yloxyimino-2-(fur-2-yl)-acetamido]-3-[(4-ethoxycarbonyl-1-methyl-1-piperazinium) methyl]ceph-3-em-4-carboxylic acid, trifluoroacetate salt (syn isomer)

(a) Diphenylmethyl (1S,6R,7R)-7-[2-t,butoxy-carbonylprop-2-yloxyimino-2-(fur-2-yl)acetamido]-3-[4-ethoxycarbonyl-1-methyl-1-piperazinium)methyl]ceph-3-em-4-carboxylate 1-oxide, iodide salt (syn isomer)

A solution of diphenylmethyl (1S,6R,7R)-3-bromomethyl-7-[2-t,butoxycarbonylprop-2-yloxyimino-2-(fur-2-yl)-acetamido]-ceph-3-em-4-carboxylate 1-oxide (syn isomer) (2.00g, 2.66 m. mole) and ethyl N-piperazinocarboxylate (0.8 ml, 2 molar equivalents) in dry tetrahydrofuran (5.5ml) was stirred at 25° C. for about 20 minutes. The reaction was monitored by t.l.c. to determine when it was complete. The reaction mixture was partitioned between ethyl acetate (150 ml) and water (250 ml) and the aqueous layer was separated and extracted with ethyl acetate (50 ml). The organic fractions were combined, washed with water (2×100ml), dried over sodium sulphate and filtered and the filtrate was evaporated to dryness. The crude product obtained was purified by column chromatography [Kieselgel 60 (silica gel-mesh size 60–200), 100g; elution with ethyl acetate (redistilled): chloroform 1:1 to 3:1]. 2.26g of diphenylmethyl (1S,6R,7R)-7-[2-t.butoxycarbonylprop-2-yloxyimino-2-(fur-2-yl)acetamido]-3-[(4-ethoxycarbonyl-1-piperazinium) methyl]ceph-3-em-4-carboxylate 1-oxide (syn isomer) were obtained; $[\alpha]_D+25°$ (c 0.24, CHCl$_3$); $\lambda_{max}$ (ethanol) 272 nm ($\epsilon$ 17,900).

2.14g of the 3-(4-ethoxycarbonyl-1-piperazinium) methyl]cephalosporin sulphoxide prepared above were stored at about 20° C. in darkness with methyl iodide (22ml) for 11 days. The reaction was monitored by t.l.c. and when reaction appeared to be complete, 250ml diethyl ether were added. The resultant gum was triturated with ether to yield the title compound (1.52g): $[\alpha]_D +22.6$ (c 0.22, CHCl$_3$); $\lambda_{max}$ (ethanol) 279 nm ($\epsilon$ 19200 and 392 nm ($\epsilon$ 5,400).

(b) Diphenylmethyl (6R,7R)-7-[2-t.-butoxycarbonylprop-2-yloxyimino-2-(fur-2-yl)acetamido]-3-[(4-ethoxycarbonyl-1-methyl-1-piperazinium)methyl]ceph-3-em-4-carboxylate, trifluoroacetate salt (syn isomer)

1.39g (1.43mmole) cephalosporin sulphoxide prepared in (a) were dissolved in acetone (3.9ml) and dry powdered potassium iodide (4 molar equivalents) was added and the mixture cooled to about $-10°$ C. Acetyl chloride (2 molar equivalent) was added. The mixture was kept at $-10°$ C. for about 5 mins. It was then allowed to warm up to about 0° C. and kept at that temperature for about 25 minutes, the reaction being monitored by t.l.c. to determine when reduction was complete. The reaction mixture was then added dropwise to a stirred solution of sodium metabisulphite (about 0.7g) in water (about 35ml) and the resultant product was separated by filtration, washed with water and dried in vacuo over phosphorus pentoxide overnight. The product was then dissolved in acetone: ethanol (9:1) and passed down a column of Deacidite FF ion exchange resin in the trifluoroacetate form, eluting with acetone: ethanol (9:1). The fractions collected which absorbed ultra-violet light were combined and evaporated to dryness to yield the title compound (1.27g); $[\alpha]_D +17.5$ (c 0.34, CHCl$_3$); $\lambda_{max}$ (ethanol) 270 nm ($\epsilon$ 18200).

(c) (6R,7R)-7-[2-Carboxyprop-2-yloxyimino-2-(fur-2-yl)-acetamido]-3-[(4-ethoxycarbonyl-1-methyl-1-piperazinium)methyl]ceph-3-em-4-carboxylic acid, trifluoroacetate salt (syn isomer)

1.16g cephalosporin diester, trifluoroacetate salt, prepared in (b) above, were mixed with anisole (1.0ml) and trifluoroacetic acid (4 ml) at 0° C. and the mixture was kept at this temperture for about 10 minutes and then allowed to warm up to room temperature over 2 hours. The volatile components of the mixture were removed in vacuo, ethyl acetate was added and was then removed in vacuo and the resultant gum was triturated with diethyl ether to give a solid product. This solid was added in portions to about 300ml of water with stirring and the resultant suspension was washed with ethyl acetate (2×150ml) and diethyl ether (150ml). The aqueous layer was separated, filtered and freeze-dried to yield a foam which on trituration with diethyl ether gave the title compound (0.626g); $[\alpha]_D$ (H$_2$O) $+41°$ (c 0.245); $\lambda_{max}$ (pH6 buffer) 277.5nm ($\epsilon$ 20,500).

EXAMPLE 2 (Method B)

(6R,7R)-7-[2-Carboxyprop-2-yloxyimino-2-(fur-2-yl) acetamido]-3-(1-methyl-1-piperidiniummethyl)ceph-3-em-4-carboxylic acid, trifluoroacetate salt (syn isomer)

(a) Diphenylmethyl (1S,6R,7R)-7-[2-t.butoxycarbonylprop-2-yloxyimino-2-(fur-2-yl)acetamido]-3-(1-methyl-1-piperidiniummethyl)ceph-3-em-4-carboxylate 1-oxide, bromide salt (syn isomer)

A solution of diphenylmethyl (1S,6R,7R)-3-bromomethyl-7-[2-t.butoxycarbonylprop-2-yloxyimino-2-(fur-2-yl) acetamido]ceph-3-em-4-carboxylate 1-oxide (syn isomer) (2.0g, 2.66m.mole) in dry tetrahydrofuran (5.5ml) was treated with N-methylpiperidine (0.33ml; 1.0 equivalents) and the mixture was stirred at 25° C. for 1 hour until the reaction was complete (as shown by t.l.c.). Diethyl ether (200ml) was added and the resulting precipitate was triturated to give the title compound, 2.03g; $[\alpha]_D$ (CHCl$_3$) $+11°$ (c 0.27); $\lambda_{max}$ (ethanol) 279 nm ($\epsilon$ 19700) and 389 nm (4400).

(b) Diphenylmethyl (6R,7R)-7-[2-t.butoxycarbonylprop-2-yloxyimino-2-(fur-2-yl)acetamido]-3-(1-methyl-1-piperidiniummethyl)ceph-3-em-4-carboxylate, trifluoroacetate salt (syn isomer)

Prepared from the cephalosporin 1-oxide obtained above analogously to Example 1(b) except that the reaction was carried out twice to ensure complete reduction; $\lambda_{max}$ (ethanol) 273 nm ($\epsilon$ 18500).

(c) (6R,7R)-7-[2-Carboxyprop-2-yloxyimino-2-(fur-2-yl) acetamido]-3-(1-methyl-1-piperidiniummethyl)ceph-3-em-4-carboxylic acid, trifluoroacetate salt (syn isomer)

Prepared from the cephalosporin diester obtained above analogously to Example 1(c); $[\alpha]_D$ (H$_2$O) $+54°$ (c 0.24); $\lambda_{max}$ (pH 6 buffer) 276.5nm ($\epsilon$ 20400).

EXAMPLES 3-12

Following the procedures described in Example 1 (Method A) and Example 2 (Method B) the (6R,7R)-7-[2-carboxyprop-2-yloxyimino-2-(fur-2-yl)acetamido]-3-(substituted)ceph-3-em-4-carboxylic acid, trifluoroacetate salts (syn isomers) listed in Table 1 which follows were prepared from (6R,7R)-3-bromomethyl-7-[2-t.butoxycarbonylprop-2-yloxyimino-2-(fur-2-yl)acetamido]-ceph-3-em-4-carboxylate 1-oxide (syn isomer) and either the appropriate secondary amine and then methyl iodide (Method A), or the appropriate N-methylamine (Method B), followed by reduction of the sulphoxide group to a sulphide group and removal of carboxyl blocking groups. Where the method differed substantially from that described in Example 1 or Example 2 this is indicated in the Table. The properties of the products are also given in the Table.

TABLE 1
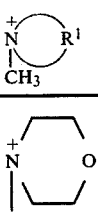
| Ex. | 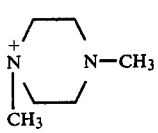 | Method | [α]$_D$(H$_2$O) | λ$_{max}$ nm (pH 6 buffer) | ε |
|---|---|---|---|---|---|
| 3 | 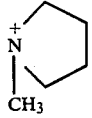 | B$^{a,e}$ | +45° (c 0.155) | 277.5 | 20200 |
| 4 | 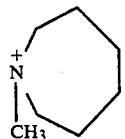 | B$^e$ | +60° (c 0.3) | 278.5 | 15800 |
| 5 | 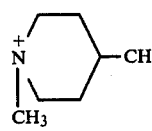 | B$^e$ | +38° (c 0.31) | 276 | 19400 |
| 6 | 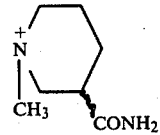 | A$^b$ | +41° (c 0.27) | 277 | 21600 |
| 7 | 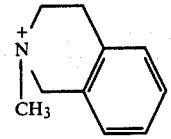 | A$^{b,f}$ | +48° (c 0.31) | 278.5<br>277 | 13100<br>20600 |
| 8 | 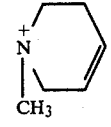 | A$^{b,h,}$ | +29.5° (c 0.27) | 276.5 | 20300 |
| 9 | 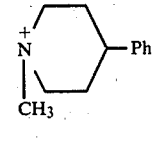 | A$^c$ | +55.5° (c 0.2) | 233<br>276 | 11800<br>20200 |
| 10 | | A$^c$ | +48° (c 0.25) | 276.5 | 20200 |
| 11 | | A$^c$ | +35° (c 0.2) | 277 | 18600 |

TABLE 1-continued

[Structure: furan-C(=N-O-C(CH3)(COOH)-CH3).CO.NH— attached to cephem nucleus with S, N, with side chain CH2-N+(CH3)(R1) and COOH; counterion CF3COO−]

| Ex. | N+(CH3)(R1) group | Method | [α]$_D$(H$_2$O) | λ$_{max}$ nm (pH 6 buffer) | ε |
|---|---|---|---|---|---|
| 12 | N+(CH3)-piperidinyl-OAc | A$^{c,d,g}$ | + 34.5° (c 0.32) | 276.5 | 20000 |
| 13 | N+(CH3)-piperidinyl-CONH2 | A $^{,i}$ | + 36.7° (c 0.3) | 276 | 19600 |
| 14 | N+(CH3)-(CH2)7 ring | A$^j$ | + 88° (c 0.25) | 277 | 18600 |

Notes $^a$The 3-(1-methyl-1-morpholiniummethyl)cephalosporin 1-oxide, bromide salt was worked up in step a) by adding water to the reaction mixture, dissolving the resultant gum in 250ml ethyl acetate, drying the organic solution over anhydrous sodium sulphate, filtering it and evaporating to dryness.

$^b$The crude product obtained in step a) by reacting the 3-bromomethyl cephalosporin 1-oxide with the secondary amine was purified by passage through a 200g column of Sorbsil eluting with redistilled ethyl acetate.

$^c$The product obtained in step a) by reacting the 3-bromomethyl cephalosporin 1-oxide with the secondary amine did not require purification before being reacted with methyl iodide.

$^d$During the reaction of the 3-bromomethyl cephalosporin 1-oxide with the secondary amine in step a) an additional 18ml acetone was added in portions to aid the solubility of the amine.

$^e$In process step b) dimethylformamide was used as solvent rather than acetone.

$^f$In process step b) two portions of acetyl chloride required to ensure complete reduction.

$^g$Displacement and quaternisation reactions were carried out on the 4-hydroxy compound which was acetylated by the acetyl chloride used in the reduction stage.

$^h$The product is a mixture of diastereoisomers.

$^i$The product obtained in step a) was purified by passage through a 25 g column of Sorbsil eluting with redistilled ethyl acetate.

$^j$The product obtained in step a) was purified by passage through a 25 g column of Sorbsil (silica gel, mesh size 60–200) eluting with 0–5% acetone in dichloromethane.

EXAMPLE 15

(6R,7R)-7-[Z-2-(1-carboxycyclobut-1-yloximino)-2-(fur-2-yl)acetamido]-3-(1,4-dimethylpiperidinium-1-ylmethyl)-ceph-3-em-4-carboxylic acid, trifluoroacetate salt (syn isomer)

(a) Diphenylmethyl (1S, 6R, 7R)-7-[(Z)-2-(1-t-butoxycarbonylcyclobut-1-yloxyimino)-2-(fur-2-yl)acetamido]-3-(4-methyl-piperidin-1-ylmethyl)ceph-3-em-4-carboxylate, 1-oxide (syn isomer)

A mixture of diphenylmethyl (1S, 6R, 7R)-3-bromomethyl-7-[(Z)-2-(1-t-butoxycarbonylcyclobut-1-yloxyimino)-2-(fur-2-yl)acetamido]ceph-3-em-4-carboxylate 1-oxide (containing ca 0.6 mole acetone) (2.13 g, 2.66 mmole) and 4-methylpiperidine (0.62 ml; 2.0 equiv.) in dry tetrahydrofuran (5.5 ml) was stirred together at 25°. Over a 5 minute period the mixture became red, gave a yellow gelatinous precipitate which dissolved to give a yellow solution. The reaction was essentially complete after 5 minutes (by t.l.c.). The reaction was worked up by pouring into water (200 ml) after 15 minutes reaction time. The resultant gum was dissolved in ethyl acetate (250 ml) and the aqueous phase was extracted with ethyl acetate (2×50 ml). The combined organic phases were washed with water (2×50 ml) and brine was added to break the emulsions formed. The organic phase was dried (anhydrous sodium sulphate) and filtered and evaporated to give the title compound (2.24 g) as a yellow foam [α]$_D$/21 +15° (c 0.4, CHCl$_3$), λ$_{max\ (ethanol)}$ 273.5nm (ε19,300).

(b) Diphenylmethyl (1S, 6R, 7R)-7-[Z-2-(1-t-butoxycarbonylcyclobut-1-yloxyimino)-2-(fur-2-yl)acetamido]-3-(1,4-dimethylpiperidinium-1-ylmethyl)ceph-3-em-4-carboxylate, 1-Oxide, Iodide salt (syn isomer)

A solution of diphenylmethyl (1S, 6R, 7R)-7-[Z-2-(1-t-butoxycarbonylcyclobut-1-yloxyimino)-2-(fur-2-yl)acetamido]-3-(4-methylpiperidin-1-ylmethyl)ceph-3-em-4-carboxylate, 1-oxide (2.12 g, 2.7 mmole) in methyl iodide (11 ml) was stored in the dark. After 3 days t.l.c. indicated that reaction was complete and ether (250 ml) was added. The resulting precipitate was triturated to give the title compound (2.204 g), as a pale yellow solid which shrinks and decomposes above 125°, [α]D/21 −4° (c 0.25, CHCl₃), λ$_{max}$ (ethanol) 281nm (ε 20,400) and 396nm (ε 3,200).

(c) Diphenylmethyl (6R, 7R)-7[Z-2-(1-t-butoxycarbonylcyclobut-1-yloxyimino)-2-(fur-2-yl)acetamido]-3-(1,4-dimethylpiperidinium-1-ylmethyl)ceph-3-em-4-carboxylate, Trifluoroacetate Salt (syn isomer)

Diphenylmethyl (1S, 6R, 7R-7-[Z-2-(1-t-butoxycarbonylcyclobut-1-yloxyimino)-2-(fur-2-yl)acetamido]-3-(1,4-dimethylpiperidinium-1-ylmethyl)ceph-3-em-4-carboxylate, 1-oxide, iodide salt (1.96 g, 2.12 mmole) and dried powdered potassium iodide (1.4 g, 4 molar equivalents) were stirred together in acetone (5.8 ml) at −10°.

Acetyl chloride (0.32 ml, 2 molar equivalents) was added and the mixture was stirred at −10° for 5 minutes, allowed to warm to 0° and then stirred at 0 to 2° for 1 hour. T.l.c. indicated that the reaction appeared to be complete. The reaction mixture was added dropwise to a stirred solution of sodium metabisulphite (1.05 g) in water (58 ml). Trituration of the resultant gum gave a solid which was filtered off, washed with water (3×10 ml) and dried in vacuo over phosphorus pentoxide to give the iodide salts of the title compound (2.126 g). A solution of this salt in acetone: ethanol (9:1) was passed down a Deacidite FF ion-exchange column (in the trifluoroacetate form); by elution with the above solvent mixture.

All fractions which (when spotted on a t.l.c. plate) absorbed ultra-violet light at 254nm were collected, combined and evaporated in vacuo to give the title salt (1.825 g), as a yellow foam, [≠]D/23+25° (c 0.156, CHCl₃), λ$_{max}$ (ethanol) 272nm (ε 17,760)

(d) (6R, 7R)-7-[Z-2-(1-Carboxycyclobut-1-ylimino)-2-(fur-2-yl)acetamido]-3-(1,4-dimethylpiperidinium-1-ylmethyl)ceph-3-em-4-carboxylic Acid Trifluoroacetate Salt (syn isomer)

A mixture of diphenylmethyl (6R, 7R)-7-[Z-2-(1-t-butoxycarbonycyclobut-1-yloxyimino)-2-(fur-2-yl)-acetamido]-3-(1,4-dimethylpiperidium-1-ylmethyl)-ceph-3-em-4-carboxylate, trifluoroacetate salt 1.69 g, 1.88 mmole), anisole (1.55 ml) and trifluoroacetic acid (6.2 ml) were stirred together at 0° for 10 minutes.

The mixture was then allowed to warm up to room temperature (25°) over 2 hours. The volatile material was removed in vacuo and the residue was azeotroped with ethyl acetate and the resultant residue was triturated with ether to give a solid (1.178 g). This solid was added portionwise to stirred water (150 ml) and the suspension was washed with ethyl acetate (2×150 ml) and ether (150 ml). The aqueous phase was filtered and freeze-dried to give a white form. Trituration of this foam with ether gave the title compound (0.855 g), as a pale yellow solid, m.p. decomposes above 155°, [α]D/23 +111° (c 0.22, H₂O), λ$_{max}$(pH6 buffer) 280nm (ε 18,200) and inflection at 266nm (ε 16,900). High pressure liquid chromatography indicated that the product was ca 69% pure with ca 27% of the corresponding Δ² isomer. R$_f$ (paper chromatography) 0.45(n-butanol:ethanol:water=4:1:5) when cephalothin has R$_f$0.6.

EXAMPLE A

This example illustrates the formulation of a pharmaceutical composition comprising the compound of Example 7 as active ingredient.

Dry powder for intravenous injection.

| Formula | Quantity per vial |
|---|---|
| Active ingredient, sterile | 500 mg |
| Anhydrous sodium citrate, sterile | q.s. to pH 6 |

Method

An aqueous solution of the sodium citrate is sterilised by membrane filtration and heated under sterile conditions to render anhydrous. The sterile anhydrous sodium citrate is milled aseptically and blended with the sterile active ingredient. The blend is then filled aseptically into glass vials under a blanket of nitrogen. The vials are closed using rubber discs or plugs held in position by aluminium sealing rings, thereby preventing gaseous exchange or ingress of micro-organisms. The product is suitable for reconstitution by dissolving in Water for Injections shortly before intravenous administration.

We claim:

1. An antibiotic compound of the formula

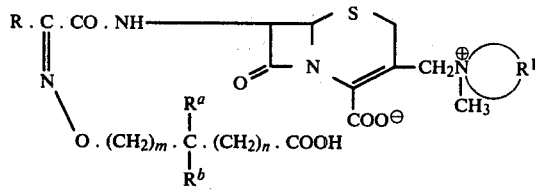

wherein R is a phenyl, thienyl or furyl group; R$^a$ and R$^b$ which may be the same or different, are individually hydrogen, C$_{1-4}$ alkyl, C$_{2-4}$ alkenyl, C$_{3-7}$ cycloalkyl, phenyl, naphthyl, thienyl, furyl or C$_{2-5}$ alkoxycarbonyl, or R$^a$ and R$^b$ together with the carbon atom to which they are attached form a C$_{3-7}$ cycloalkylidene or cycloalkenylidene group; m or n are each 0 or 1 such that the sum of m and n is 0 or 1; and R$^1$ together with the nitrogen atom to which it is attached form a saturated or partially saturated 4–10 membered unsubstituted heterocyclic ring having 0 or 1 further heteroatom selected from O, N and S in addition to the carbon atoms, or such a heterocyclic ring substituted by a lower alkyl, lower alkoxy, lower carboxylic acyloxy, lower alkoxycarbonyl, hydroxy, carboxy, amino, carbamoyl or phenyl group, or such a heterocyclic ring fused with a benzene ring; or a non-toxic salt, biologically acceptable ester, 1-oxide or solvate thereof, said antibiotic compound being a syn isomer or existing as a mixture of syn and anti isomers.

2. A compound as claimed in claim 1 existing as a mixture of syn and anti isomers containing at least 75% of the syn isomer.

3. A compound as claimed in claim 1 which is a syn isomer essentially free from the anti isomer.

4. A compound as claimed in claim 1 in which m and n are 0, R$^a$ and R$^b$ are hydrogen, methyl, ethyl, propyl, allyl or phenyl; or R$^a$ and R$^b$ together with the carbon atom to which they are attached form a cyclobutylidene, cyclopentylidene or cyclohexylidene ring.

5. A compound as claimed in claim 1 in which R represents a fur-2-yl group.

6. A compound as claimed in claim 1 in which $R^1$ together with the nitrogen atom to which it is attached represents a saturated or monosaturated 5-, 6-, 7- or 8-membered unsubstituted heterocyclic ring having 0 or 1 further heteroatom selected from O and N in addition to the carbon atoms or such a heterocyclic ring substituted by a methyl, carbamoyl, ethoxycarbonyl, acetoxy or phenyl group, or such a heterocyclic ring fused with a benzene ring.

7. A compound as claimed in claim 1, being (6R,7R)-7-[2-(2-carboxyprop-2-yloxyimino)-2-fur-2-yl)-acetamido]-3-[(4-ethoxycarbonyl-1-methyl-1-piperazinium)methyl]ceph-3-em-4-carboxylate (syn isomer) or a non-toxic addition salt thereof.

8. A compound as claimed in claim 1, being (6R,7R)-7-[2-(2-carboxyprop-2-yloxyimino)-2-(fur-2-yl)-acetamido]-3-(1-methyl-2-hexamethyleneiminiummethyl)ceph-3-em-4-carboxylate (syn isomer) or a non-toxic acid addition salt thereof.

9. A compound as claimed in claim 1, being 6R,7R)-7-[2 (2-carboxyprop-2-yloxyimino)-2-(fur-2-yl)-acetamido]-3-[(1,4-dimethyl-1-piperidinium)methyl]-ceph-3-em-4-carboxylate (syn isomer) or a non-toxic acid addition salt thereof.

10. A compound as claimed in claim 1, being (6R,7R)-7-[2-(2-carboxyprop-2-yloxyimino)-2-(fur-2-yl)-acetamido]-3-[(3-carbamoyl-1-methyl-1-piperidinium)methyl]-ceph-3-em-4-carboxylate (syn isomer) or a non-toxic acid addition salt thereof.

11. A compound as claimed in claim 1, being (6R,7R)-7-[2-(2-carboxyprop-2-yloxyimino)-2-(fur-2-yl)-acetamido]-3-(1-methyl-1,2,3,6-tetrahydropyridinium-1-yl-methyl)ceph-3-em-4-carboxylate (syn isomer) or a non-toxid acid addition salt thereof.

12. A compound as claimed in claim 1, being (6R,7R)-7-[2-(2-carboxyprop-2-yloxyimino)-2-(fur-2-yl)-acetamido]-3-(4-acetoxy-1-methyl-1-piperidiniummethyl)-ceph-3-em-4-carboxylate (syn isomer) or a non-toxic acid addition salt thereof.

13. A compound as claimed in claim 1, being (6R,7R)-7-[2-(2-carboxyprop-2-yloxyimino)-2-(fur-2-yl)-acetamido]-3-(4-carbamoyl-1-methyl-1-piperidiniummethyl)-ceph-3-em-4-carboxylate (syn isomer) or a non-toxic acid addition salt thereof.

14. A compound as claimed in claim 1, being (6R,7R)-7-[2-(2-carboxyprop-2-yloxyimino)-2-(fur-2-yl)-acetamido]-3-(1-methyloctahydroazocinium-1-ylmethyl)ceph-3-em-4-carboxylate (syn isomer) or a non-toxic acid addition salt thereof.

15. A compound as claimed in claim 1, being (6R,7$)-7-[2-(2-carboxyprop-2-yloxyimino)-2-(fur-2-yl)acetamido]-3-[1-methyl-pyrrolidinium-1-ylmethyl]-ceph-3-em-4-carboxylate (syn isomer) or a non-toxic acid addition salt thereof.

16. A compound as claimed inclaim 1, being (6R,7R)-7-[2-(1-carboxycyclobut-1-yloximino)-2-(fur-2-yl)acetamido]-3-(1,4-dimethylpiperidinium-1-ylmethyl)ceph-3-em-4-carboxylate (syn isomer) or a non-toxic acid addition salt thereof.

17. A pharmaceutical composition comprising an antibiotic compound as claimed in claim 1 together with a pharmaceutical carrier or excipient.

* * * * *